United States Patent [19]
Insall et al.

[11] Patent Number: 5,830,216
[45] Date of Patent: Nov. 3, 1998

[54] APPARATUS AND METHOD FOR KNEE IMPLANTATION

[75] Inventors: John N. Insall, New York; Giles R. Scuderi, Garden City, both of N.Y.; Pascal Poilvache, Brussels, Belgium; Robert A. Hodorek, Warsaw, Ind.; David J. Krueger, Austin, Tex.

[73] Assignee: Bristol-Myers Squibb Company, New York, N.Y.

[21] Appl. No.: 742,427

[22] Filed: Oct. 30, 1996

[51] Int. Cl.⁶ ................................................ A61B 17/58
[52] U.S. Cl. ............................................. 606/88; 606/87
[58] Field of Search ........................................ 606/88, 87

[56] References Cited

U.S. PATENT DOCUMENTS

| | | | |
|---|---|---|---|
| D. 272,854 | 2/1984 | Witte et al. | D24/26 |
| D. 273,895 | 5/1984 | Kenna | D24/26 |
| D. 274,090 | 5/1984 | Kenna | D24/26 |
| D. 274,091 | 5/1984 | Kenna | D24/26 |
| D. 274,092 | 5/1984 | Kenna | D24/26 |
| D. 274,161 | 6/1984 | Kenna | D24/26 |
| D. 274,162 | 6/1984 | Kenna | D24/26 |
| D. 355,254 | 2/1995 | Kraft et al. | D24/140 |
| D. 367,706 | 3/1996 | Stalcup et al. | D24/140 |
| 4,474,177 | 10/1984 | Whiteside | 128/303 R |
| 4,487,203 | 12/1984 | Androphy | 128/303 R |
| 4,502,483 | 3/1985 | Lacey | 128/303 R |
| 4,524,766 | 6/1985 | Petersen | 128/92 H |
| 4,646,729 | 3/1987 | Kenna et al. | 128/92 VW |
| 4,653,488 | 3/1987 | Kenna | 128/92 VW |
| 4,703,751 | 11/1987 | Pohl | 128/92 VW |
| 4,722,330 | 2/1988 | Russell et al. | 128/92 VW |
| 4,738,253 | 4/1988 | Buechel et al. | 128/92 VW |
| 4,738,254 | 4/1988 | Buechel et al. | 128/92 VW |
| 4,759,350 | 7/1988 | Dunn et al. | 128/92 VW |
| 4,787,383 | 11/1988 | Kenna | 128/303 R |
| 4,791,919 | 12/1988 | Elloy et al. | 128/92 VW |
| 4,825,857 | 5/1989 | Kenna | 128/92 VW |
| 4,841,975 | 6/1989 | Woolson | 128/653 |

(List continued on next page.)

FOREIGN PATENT DOCUMENTS

| | | | |
|---|---|---|---|
| 380451 | 8/1990 | European Pat. Off. | 606/88 |
| WO 94/33413 | 5/1995 | WIPO | A61B 17/17 |

OTHER PUBLICATIONS

Zimmer, Inc.—Insall/Burstein Posterior Stabilized II Modular Knee System Brochure—c1989—Lit. No. 97–5220–02.

Zimmer, Inc.—NexGen® Complete Knee Solution Brochure—c1995—Lit. No. 97–5970–102 Rev. 1.

*Primary Examiner*—Michael Buiz
*Assistant Examiner*—Julian W. Woo
*Attorney, Agent, or Firm*—Cary R. Reeves

[57] ABSTRACT

A set of instruments and a surgical technique facilitate precise orientation of the femoral implant. Precision is aided by decoupling the determination of A/P placement, valgus angle, and external rotation into three discrete steps. In this way, a surgeon's full concentration can be directed to each element of placement and fine adjustments can readily be made to each. An Epicondylar Guide is configured to ease referencing external rotation from the epicondyles. The narrow elongated guide is easily alignable with the epicondyles when it is placed on the flat distal cut. A Posterior Reference/Rotation Guide can be attached to the Epicondylar Guide to check the rotation relative to the intact posterior condyles to confirm the epicondylar setting. A slot in the guide guides a saw blade to cut a corresponding slot in the distal femur. An A/P Cutting Guide has a fin that fits in the slot cut in the distal femur. With the A/P Cutting Guide engaging the slot and resting on the flat distal cut, external rotation is fixed and the A/P Cutting Guide can only move in the A/P direction. By moving the guide in the A/P direction, fine adjustments in the flexion and extension gaps can be made. Once A/P placement is set, the anterior and posterior cuts are made through slots in the guide. In an alternative embodiment, the Epicondylar Guide defines a linear track attached to the distal femur and the A/P Cutting Guide includes a slot configured to engage the linear track.

15 Claims, 12 Drawing Sheets

U.S. PATENT DOCUMENTS

| | | | |
|---|---|---|---|
| 4,892,093 | 1/1990 | Zarnowski et al. | 606/82 |
| 4,907,578 | 3/1990 | Petersen | 606/79 |
| 4,938,762 | 7/1990 | Wehrli | 606/88 |
| 4,944,760 | 7/1990 | Kenna | 623/20 |
| 5,002,547 | 3/1991 | Poggie et al. | 606/88 |
| 5,037,423 | 8/1991 | Kenna | 606/88 |
| 5,053,037 | 10/1991 | Lackey | 606/79 |
| 5,100,408 | 3/1992 | Lackey | 606/79 |
| 5,116,338 | 5/1992 | Poggie et al. | 606/90 |
| 5,122,144 | 6/1992 | Bert et al. | 606/88 |
| 5,129,909 | 7/1992 | Sutherland | 606/88 |
| 5,250,050 | 10/1993 | Poggie et al. | 606/79 |
| 5,282,803 | 2/1994 | Lackey | 606/80 |
| 5,364,401 | 11/1994 | Ferrante et al. | 606/84 |
| 5,405,349 | 4/1995 | Burkinshaw et al. | 606/88 |
| 5,411,505 | 5/1995 | Mumme | 606/88 |
| 5,415,633 | 5/1995 | Luckman et al. | 606/86 |
| 5,417,693 | 5/1995 | Sowden et al. | 606/85 |
| 5,417,694 | 5/1995 | Marik et al. | 606/88 |
| 5,423,822 | 6/1995 | Hershberger et al. | 606/79 |
| 5,423,827 | 6/1995 | Mumme et al. | 606/96 |
| 5,445,642 | 8/1995 | McNulty et al. | 606/88 |
| 5,454,816 | 10/1995 | Ashby | 606/88 |
| 5,458,645 | 10/1995 | Bertin | 623/20 |
| 5,464,406 | 11/1995 | Ritter et al. | 606/86 |
| 5,474,559 | 12/1995 | Bertin et al. | 606/89 |
| 5,484,446 | 1/1996 | Burke et al. | 606/87 |
| 5,486,178 | 1/1996 | Hodge | 606/82 |
| 5,490,854 | 2/1996 | Fisher et al. | 606/88 |
| 5,490,855 | 2/1996 | Bouraly et al. | 606/88 |
| 5,569,261 | 10/1996 | Marik et al. | 606/88 |

APPARATUS AND METHOD FOR KNEE IMPLANTATION

BACKGROUND OF THE INVENTION

The present invention relates to instruments for preparing the human femur for receiving a femoral knee implant. More specifically, the present invention relates to a set of instruments for making highly precise anterior and posterior femoral bone cuts.

Figure 1:
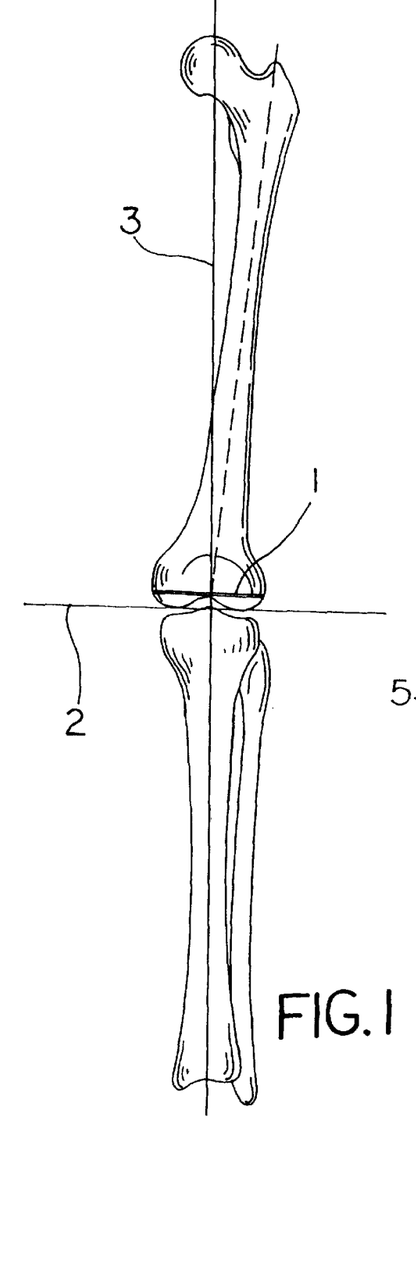
FIG. 1 is a front plan view of a femur and a tibia showing various axes of the knee joint.
Figure 2:
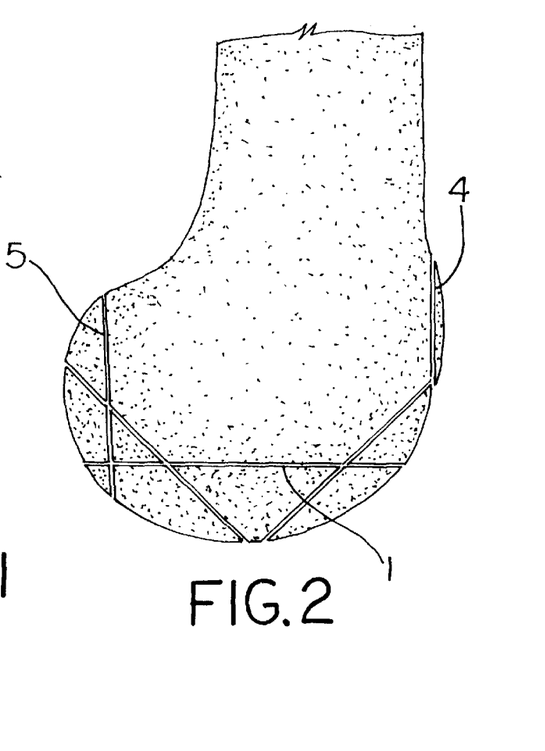
FIG. 2 is a side section view of the distal femur showing the bone cuts which are necessary to prepare the femur to receive a prosthetic implant.

The implantation of a femoral knee implant involves establishing three critical aspects of the implant's orientation as shown in FIGS. 1–2. First, the valgus angle is determined by the angle of the distal cut 1 from side to side relative to the transverse axis 2. The valgus angle is important in establishing proper load transfer to the medial and lateral compartments of the knee joint. Second, the external rotation, which is the rotation of the implant about the longitudinal axis 3, is fixed by the rotation of the anterior 4 and posterior 5 cuts about the longitudinal axis 3. External rotation affects the patellar tracking of the joint. Third, anterior-to-posterior (A/P) placement, which is the positioning of the implant in the A/P direction, is determined by the A/P position of the anterior 4 and posterior 5 cuts. The A/P placement of the implant affects the tension of the knee joint in flexion. This aspect of implant placement is sometimes referred to as the flexion gap.

Different means for establishing these three critical aspects of orientation have been proposed. An exemplary system is the Insall/Burstein® II Modular Knee System sold by Zimmer, Inc. As detailed in the surgical technique published for the posterior stabilized implants in this system, a rod extending from an intramedullary alignment guide is inserted into the distal end of the uncut femur. The alignment guide is rotated until it is parallel to the cut surface of the tibia or alternatively until it is parallel to the posterior condyles. An anterior femoral cutting guide is placed on the femoral alignment guide and the anterior femoral rough cut is made. This cut establishes the external rotation for the femoral implant because the subsequent final A/P cuts are made by referencing from this initial cut. The A/P placement of the implant is also determined by this first cut. The A/P position of the cut is determined by an anterior locating boom that extends over and rests its tip on the anterior femur. The A/P position of the final A/P cuts are referenced from this initial cut. The valgus angle is determined by placing the distal femoral cutting guide on the I/M alignment guide and pinning it at the desired valgus angle by referencing a scale on the cutting guide. When the distal femur is resected, the valgus angle is fixed.

Another exemplary knee system is detailed in the surgical technique published by Zimmer, Inc. for the cruciate retaining (CR) implants in the NexGen™ Complete Knee Solution. This technique corresponds to the NexGen CR femoral implants. In this system, the first step is sizing the femur with a femoral sizing guide having an intramedullary rod, a boom for contacting the anterior femoral cortex and feet for contacting the posterior condyles. With the guide in place, external rotation can be marked on the femur by drilling through a set of holes provided in the guide. The indicia adjacent the holes indicate the amount of rotation relative to the feet contacting the posterior condyles. After the femoral sizing guide is removed, an I/M alignment guide having an I/M rod extending from a base and handles extending from the base perpendicular to the I/M rod is inserted into the femur. The base of the I/M alignment guide can be angled to different predetermined valgus angles.

With the desired valgus angle locked into the guide, the guide is rotated to the desired external rotation. The external rotation can be set by aligning the guide with the holes drilled during the sizing step. Alternatively, the external rotation can be set by aligning the handles to be parallel with the cut tibia or to be parallel to an imaginary line through the epicondyles of the femur. A/P placement is established with an A/P positioning guide which is attached to the alignment guide and which gauges the position with an anterior boom that contacts the anterior femoral cortex. With the external rotation, valgus angle, and A/P placement established, mounting bases are attached to the femur and the guides are removed. Milling or cutting guides are attached to the mounting bases and milling or cutting of the femoral cuts is carried out.

These examples have described three landmarks which can be used in establishing external rotation. The first is available when the proximal tibial surface has been resected prior to preparation of the femur. In this case an intramedullary guide inserted into the femur can be rotated until it is parallel to the proximal tibial surface. This landmark sets the femoral external rotation to match the angle cut into the tibia. The second landmark is the posterior femoral condyles. When the posterior condyles are not deformed, the guide can be rotated so that it is parallel to the condyles, or in other words so that equal amounts of the posterior condyles are visible. This landmark sets the external rotation to match the anatomic external rotation of the posterior condyles. The third landmark is the epicondyles of the femur. The epicondyles are projections from the femur located proximal to the medial and lateral condyles. The epicondyles can be palpated and it has been found that a line through the epicondyles, or epicondylar axis, corresponds well to the rotational axis of the knee. To use this landmark, the I/M guide is rotated to be parallel to the epicondylar axis.

SUMMARY OF THE INVENTION

The present invention provides a set of instruments and a surgical technique that facilitate precise orientation of the femoral implant. Precision is aided by decoupling the determination of A/P placement, valgus angle, and external rotation into three discrete steps. In this way, a surgeon's full concentration can be directed to each element of placement and fine adjustments can readily be made to each. The valgus angle is set first and the distal femoral cut is made using a Distal Femoral Cutting Guide. A preferred Distal Femoral Cutting Guide makes the distal femoral cut correspond to 3° of flexion of the femur. An Epicondylar Guide is configured to ease referencing external rotation from the epicondyles. The narrow elongated guide is easily alignable with the epicondyles when it is placed on the flat distal cut. Its trim shape permits good visualization. The guide is aligned with the epicondylar axis. A Posterior Reference/Rotation Guide can be attached to the Epicondylar Guide to check the rotation relative to the intact posterior condyles to confirm the epicondylar setting. A slot in the guide guides a saw blade to cut a corresponding slot in the distal femur. The Epicondylar Guide is removed. An A/P Cutting Guide has a fin that fits in the slot cut in the distal femur. With the A/P Cutting Guide engaging the slot and resting on the flat distal cut, external rotation is fixed and the A/P Cutting Guide can only move in the A/P direction. The A/P Cutting Guide has an anterior boom that indicates the resection level for the anterior flange and that can be used for setting A/P placement. By moving the guide in the A/P direction, fine adjustments in the flexion gap can be made. Once A/P placement is set, the anterior and posterior cuts are made through slots in the guide. The 3° of flexion of the distal femoral cut helps to prevent notching of the anterior femur when the A/P placement is adjusted posteriorly.

In an alternative embodiment, the Epicondylar Guide comprises a central block defining a linear track and the A/P Cutting Guide comprises a body that engages the linear track. In this embodiment, the Epicondylar Guide is positioned on the distal femur and pinned in place. The A/P Cutting Guide is engaged with the linear track and moved in the A/P direction to the desired position before the anterior and posterior femoral cuts are made.

DETAILED DESCRIPTION OF THE INVENTION

Figure 3:
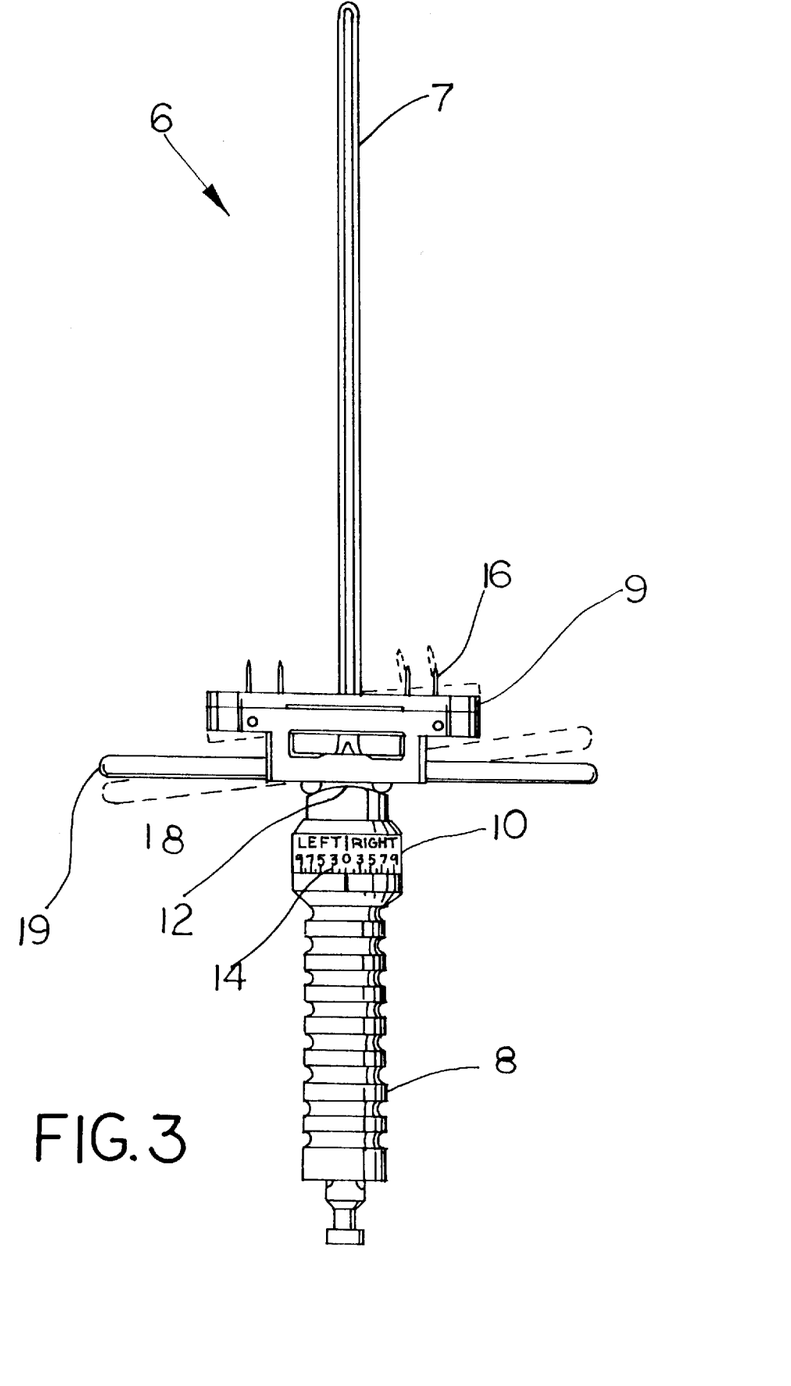
FIG. 3 is front plan view of an IM Alignment Guide.

Referring to FIG. 3, an IM Alignment Guide 6 has an IM rod 7 and a handle 8 oriented along a longitudinal axis. A base 9 is mounted on the handle 8 and IM rod 7 so that it can pivot about an axis normal to the longitudinal axis. A valgus angle adjustment knob 10 is mounted on the handle 8 for rotation about the longitudinal axis. The valgus angle adjustment knob 10 has a cam surface 12 that engages the base 9. When the valgus angle adjustment knob 10 is rotated, the cam surface 12 causes the base 9 to pivot about the axis normal to the longitudinal axis. The base 9 forms an angle with the longitudinal axis that varies with the rotational position of the valgus angle adjustment knob 10. The valgus angle adjustment knob 10 includes indicia 14 for indicating the angle of the base 9 relative to the IM rod 7. Pins 16 for engaging bone protrude distally from the base 9. A slot 18 is formed in the base 9 for engaging other instruments. The slot 18 provides an opening in the base 9 extending into the base 9 perpendicular to the longitudinal axis. A pair of arms 19 extend laterally from the base 9 perpendicular to the slot 18.

Figures 4, 5, 6, 7, 8, 9, 10:
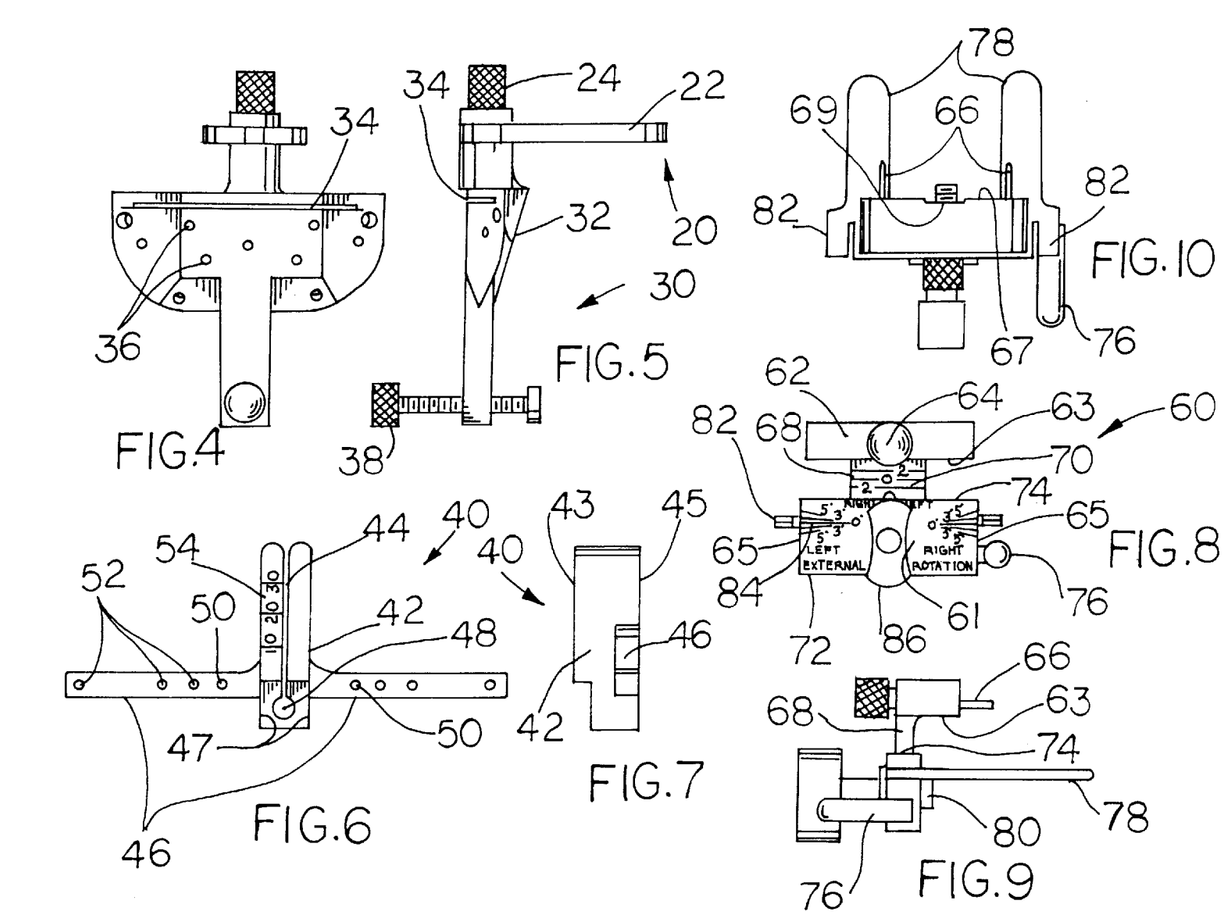
FIG. 4 is a front plan view of a Distal Placement Guide assembled with a Distal Femoral Cutting Guide according to the present invention.
FIG. 5 is a side plan view of the Distal Placement Guide assembled with the Distal Femoral Cutting Guide of FIG. 4.
FIG. 6 is a front plan view of an Epicondylar Guide according to the present invention.
FIG. 7 is a side plan view of the Epicondylar Guide of FIG. 6.
FIG. 8 is a front plan view of a Posterior Reference/Rotation Guide according to the present invention.
FIG. 9 is a side plan view of the Posterior Reference/Rotation Guide of FIG. 8.
FIG. 10 is a top plan view of the Posterior Reference/Rotation Guide of FIG. 8.

FIGS. 4 and 5 depict a Distal Placement Guide 20 coupled with a Distal Femoral Cutting Guide 30. The Distal Placement Guide 20 includes an arm 22 and an attachment screw 24. The arm 22 is shaped to engage the slot 18 in the IM Alignment Guide base 9 in a close sliding fit. The Distal Femoral Cutting Guide 30 includes a body 32. The body 32 has a threaded attachment hole for receiving the attachment screw 24. A distal cutting slot 34 extends through the body 32. Fixation holes 36 also extend through the body 32. An anterior thumb screw 38 extends through the body 32 in threaded engagement with the body 32 so that rotation of the thumb screw 38 changes the spacing of the ends of the thumb screw 38 from the body 32. The Distal Placement Guide 20 is attached to the Distal Femoral Cutting Guide 30 threading the attachment screw 24 into the threaded attachment hole and tightening the attachment screw 24. The Distal Placement Guide/Distal Femoral Cutting Guide assembly is positioned on the IM Alignment Guide by sliding the arm 22 into the slot 18. With these three parts assembled, the distal cutting slot 34 defines a cutting plane that is angled relative to the IM rod 4. Two Distal Placement Guides 20 are provided. One positions the distal cutting slot 34 at an angle of 0° relative to the IM rod 4 and the other positions the distal cutting slot 34 at an angle of 3° relative to the IM rod 4.

FIGS. 6 and 7 depict an Epicondylar Guide 40. The Epicondylar Guide 40 includes a central block 42 having a front side 43, a back side 45 and edges 47. An elongated A/P slot 44 extends through the central block 42 from front 43 to back 45. Slender, elongated, epicondylar reference arms 46 extend from the central block 42 perpendicular to the A/P slot 44. A threaded attachment hole 48 is formed in the central block 42. Alignment holes 50 and fixation holes 52 are formed on the Epicondylar Guide 40 with the fixation holes 52 extending through the Epicondylar Guide 40. The central block 42 is 22 mm from front 43 to back 45. A measurement scale 54 is inscribed on a surface of the Epicondylar Guide 40. The scale 54 is used as a reference to place a mark, such as with a piece of tape, on a saw blade 30 mm from the blade tip. Thus when the blade is inserted into the A/P slot 44 to the mark, it extends 8 mm from the guide to produce an 8 mm slot in the underlying bone.

FIGS. 8–10 depict a Posterior Reference/Rotation Guide 60. The Posterior Reference/Rotation Guide 60 includes a body 62 having a back surface 67 and a bottom surface 63. The back surface 67 includes a chamfered notch 69. The body 62 carries an attachment screw 64 and alignment pins 66. A neck 68 extends from the bottom surface 63. The neck 68 includes a femoral A/P position scale 70 preferably comprising multiple marks spaced 2 mm apart. A first mark is labeled "0". A second mark, 2 mm from the first mark and closer to the bottom surface 63, is labeled "2". A third mark, 2 mm from the first mark and further away from the bottom surface 63, is labeled "2". A sliding member 72 slidingly engages the neck 68. The sliding member 72 has a top surface 74, a front surface 61 and sides 65. The top surface 74 opposes the bottom surface 63. The sliding member 72 is slidable from a first position in which the bottom surface 63 and top surface 74 are near one another and a second position in which the bottom surface 63 and top surface 74 are spaced from one another. The sliding member 72 obscures portions of the femoral position scale 70 as it slides along the neck 68. By sighting along the top surface 74 of the sliding member 72, the position of the sliding member 72 relative to the femoral position scale 70 can be determined. A locking lever 76 threadingly engages the sliding member 72 and bears against the neck 68 so that when the locking lever 76 is tightened the sliding member 72 is prevented from sliding along the neck 68. A pair of posterior paddle feet 78 are rotatably mounted by a pivot 80 on the sliding member 72. The pivot 80 axis is parallel to the top surface 74 and is located midway between the feet 78 which rotate as a pair about the pivot 80. The feet 78 are flat plates with their top surfaces lying in a common plane parallel to the pivot 80 axis. Lateral extensions 82 extend from the feet 78 and project adjacent the sides 65 of the sliding member. An external rotation scale 84 is marked on the front surface 61 of the sliding member 72. The external rotation scale 84 comprises multiple marks angled relative to one another adjacent each side 65 of the sliding member 72. A first mark on each side is labeled "0°" and corresponds to the horizontal position of the feet 78. Subsequent marks are positioned on each side at 3 and 5 degrees above and below the "0°" mark and are labeled "3°" and "5°" accordingly. The sets of marks are further labeled to indicate left and right knees. The marks on the left have the word "LEFT" inscribed below the angle marks and the word "RIGHT" inscribed above the angle marks. The marks on the right have the word "RIGHT" inscribed below the angle marks and the word "LEFT" inscribed above the angle marks. A rotation lock 86 locks the pivot 80. When the rotation lock 86 is activated by rotating it clockwise, the feet 78 are prevented from rotating relative to the sliding member 72.

The Posterior Reference/Rotation Guide 60 can be mounted on the Epicondylar Guide 40. The attachment screw 64 threads into the threaded attachment hole 48. With the attachment screw 64 tightened, the Posterior Reference/Rotation Guide 60 is rigidly fixed to the Epicondylar Guide 40. The chamfered notch 69 seats against the edges 47 so that the Posterior Reference/Rotation Guide 60 is consistently mounted without rotation relative to the Epicondylar Guide 40. When the feet 78 are in the horizontal position, the tops of the feet are in a plane perpendicular to the A/P slot 44 of the Epicondylar Guide 40 and the lateral extensions are aligned with the "0°" marks on the external rotation scale 84. When the feet 78 are rotated 93 degrees down to the left relative to the A/P slot 44, the lateral extensions align with the left "3°" mark below the "0°" mark corresponding to the quadrant labeled "LEFT" and the right "3°" mark above the "0°" mark corresponding to the quadrant labeled "LEFT". This position of the lateral extensions thus indicates a left knee in 3° of external rotation. The lateral extensions 82 and the external rotation scale 84 similarly align to indicate the position of the feet 78 relative to the A/P slot at 3 and 5 degrees above and below the horizontal.

Figures 11, 12, 13, 14, 15:
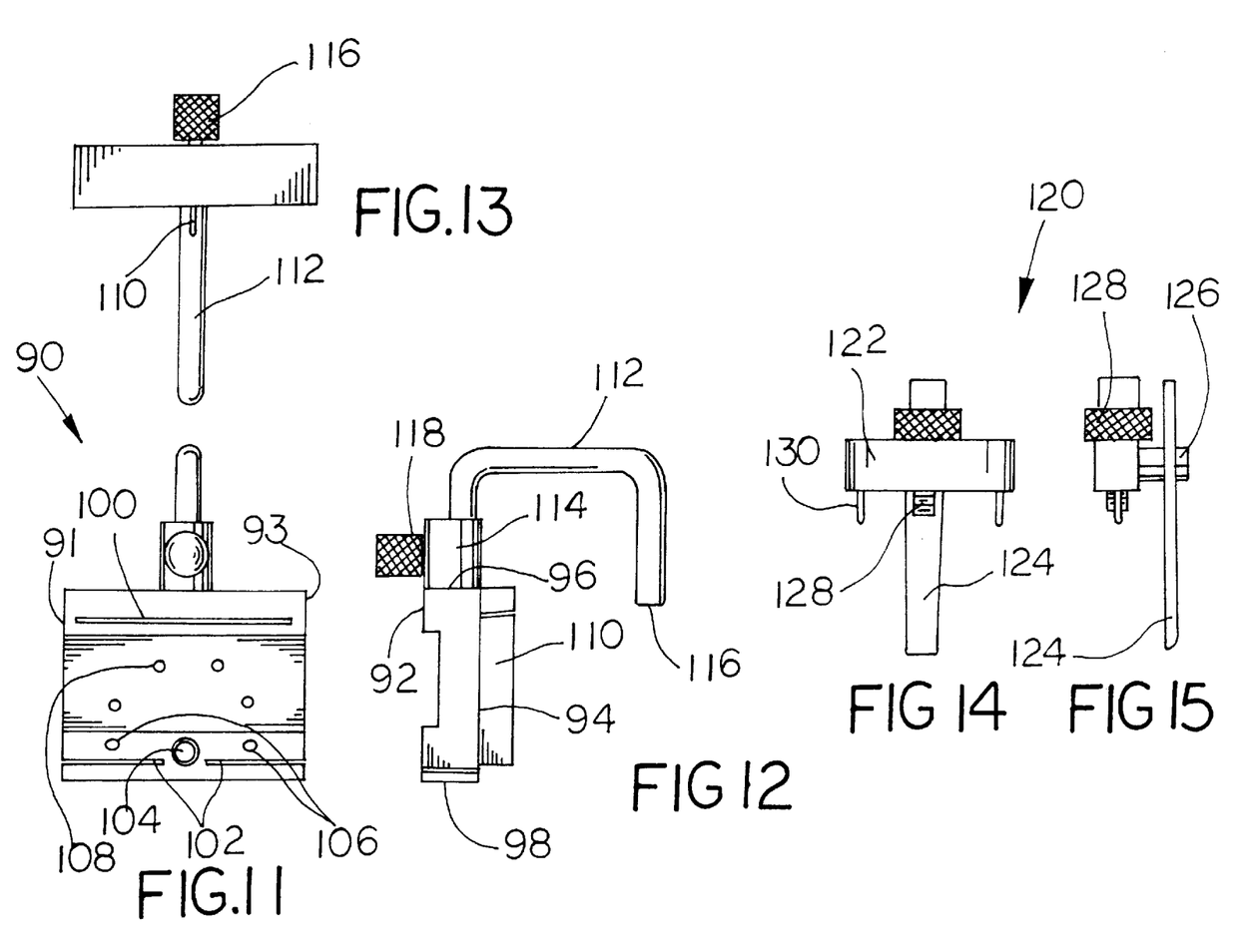
FIG. 11 is a front plan view of an A/P Cutting Guide according to the present invention.
FIG. 12 is a side plan view of the A/P Cutting Guide of FIG. 11.
FIG. 13 is a bottom plan view of the A/P Cutting Guide of FIG. 11.
FIG. 14 is a front plan view of a Posterior Resection Gauge according to the present invention.
FIG. 15 is a side plan view of the Posterior Resection Gauge of FIG. 14.

FIGS. 11–13 depict an A/P Cutting Guide 90. The A/P Cutting Guide 90 includes a cutting block 91 having front 92, back 94, top 96, bottom 98, left 91 and right 93 sides. Anterior 100 and posterior 102 cutting slots extend through the cutting block from front 92 to back 94 perpendicular to the back 94. The cutting slots 100 and 102 are elongated in the front 92 and back 94 sides and extend from near the left side 91 to near the right side 93. A threaded attachment hole 104 is formed in the cutting block 91. The threaded attachment hole 104 interrupts the posterior cutting slot 102. Alignment holes 106 and fixation holes 108 are formed on the cutting block 91 with the fixation holes 108 extending through the cutting block 91. A fin 110 projects from the back side 94 of the cutting block 91 normal to the back side 94 and perpendicular to the elongated cutting slots 100 and 102. An anterior boom 112 is pivotally mounted on the top side 96 in a bearing 114. The boom is "U" shaped with one end of the "U" being mounted in the bearing 114 and the other end, or probe end 116 lying in a plane parallel to the cutting slots 100 and 102. As the boom 112 is rotated about the bearing 114, the probe end 116 remains in a plane parallel to the cutting slots 100 and 102. A locking screw 118 threads into the wall of the bearing 114 and prevents the boom 112 from rotating in the bearing 114 when it is tightened.

The Posterior Reference/Rotation Guide 60 (FIGS. 8–10) can be mounted on the A/P Cutting Guide 90 (FIGS. 11–13). Alignment pins 66 engage the alignment holes 106 and the attachment screw 64 threads into the threaded attachment hole 104. With the attachment screw 64 tightened, the Posterior Reference/Rotation Guide 60 is rigidly fixed to the A/P Cutting Guide 90. When the feet 78 are in the horizontal position, the tops of the feet are in a plane parallel to the planes of the cutting slots 100 and 102 and perpendicular to the fin 110. The external rotation scale 84 and lateral extensions 82 indicate the angle of the feet 78 relative to the cutting slots 100 and 102 and the fin 110. The femoral position scale 70 indicates the A/P position of the feet 78 relative to the probe end 116.

FIGS. 14 and 15 depict a Posterior Resection Gauge 120. The Posterior Resection Gauge 120 includes a gauge body 122 and a wing 124 rotatably mounted to the gauge body 122 at a pivot 126. The gauge body 122 carries an attachment screw 128 and alignment pins 130. The Posterior Resection Gauge 120 can be mounted on the A/P Cutting Guide 90. Alignment pins 130 engage the alignment holes 106 and the attachment screw 128 threads into the threaded attachment hole 104. With the attachment screw tightened, the Posterior Resection Guide 120 is rigidly fixed to the A/P Cutting Guide 90. The wing 124 rotates in a plane that is a predetermined distance from the probe end 116.

Figure 16:
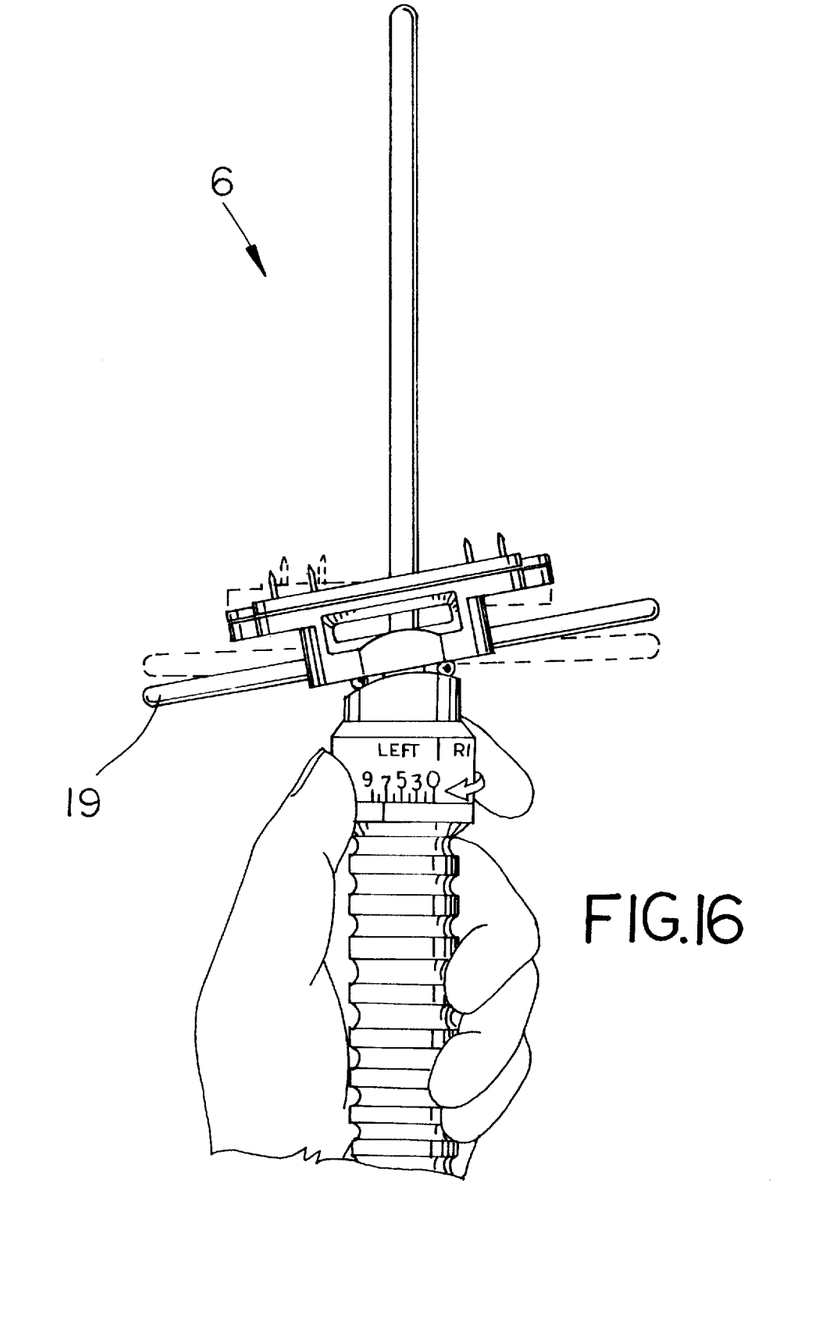
FIG. 16 is a front plan view of the IM Alignment Guide of FIG. 3 showing how it is adjusted for valgus angle.

FIGS. 16–29 depict the use of the above instruments. First, a hole is drilled in the distal femur collinear with the intramedullary canal. The IM Alignment Guide 6 is set to the desired valgus angle (FIG. 16) and it is inserted into the hole. If a distal placement guide establishing 3° of flexion will be used, the rotation of the IM Alignment Guide should be set using the epicondylar axis by positioning the arms 19 of the guide relative to the epicondyles. This does not set external rotation, but keeps the distal cut properly oriented to the final component rotation. If a distal placement guide establishing 0° of flexion will be use, then rotation of the IM Guide need not be considered. The IM Alignment Guide 6 is then seated on the most prominent condyle.

Figure 17:
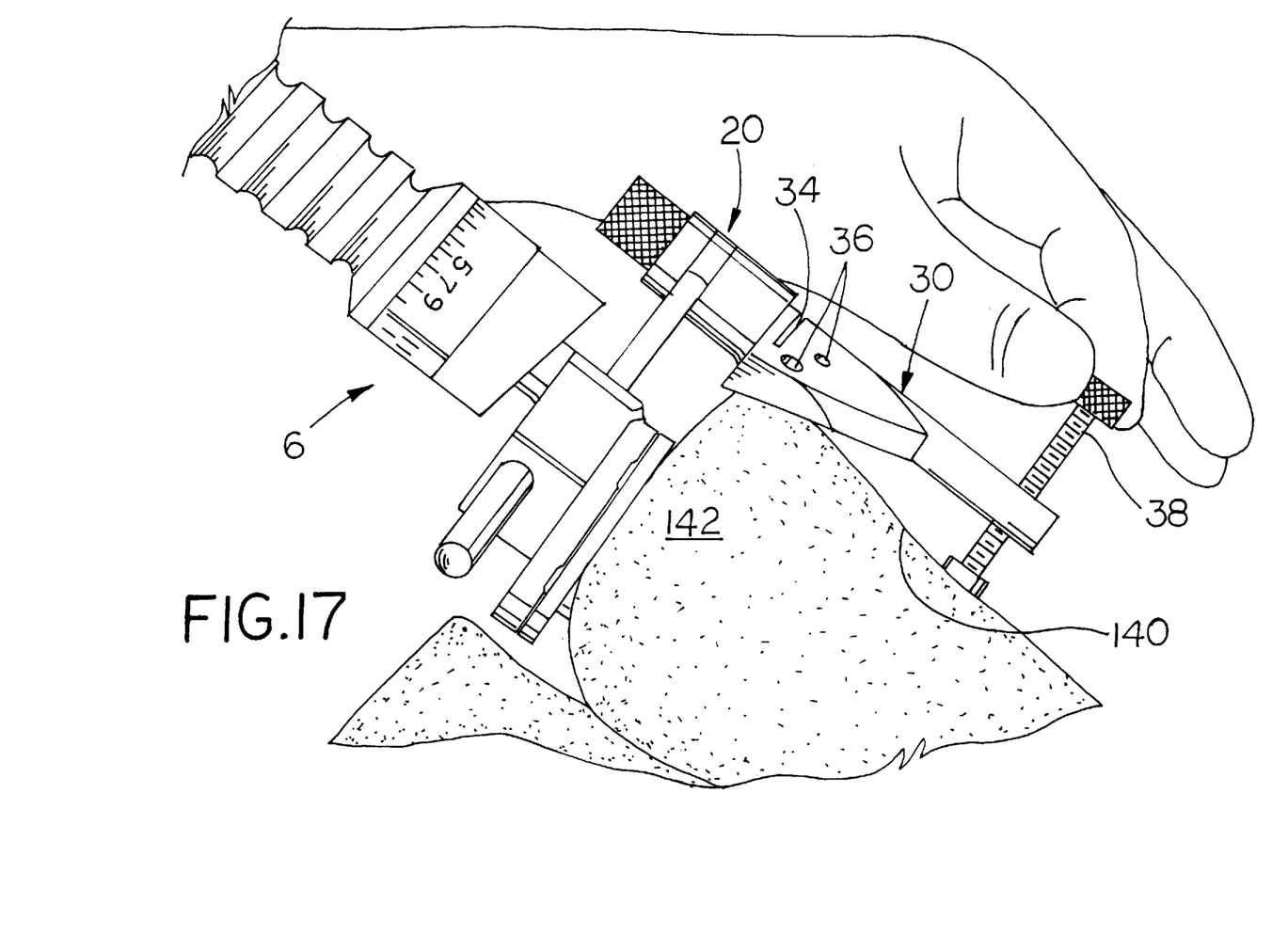
FIG. 17 is a perspective view of the IM Alignment Guide of FIG. 3 inserted into the femur and carrying the Distal Placement Guide and Distal Femoral Cutting Guide of FIG. 4.

Next, the Distal Femoral Cutting Guide 30 is attached to the Distal Placement Guide 20. Normally, the 3° Distal Placement Guide 20 will be used since 3° of flexion affords protection against notching of the anterior femoral cortex. This is especially important when the A/P position, which is set in a subsequent step, is adjusted posteriorly. The Distal Placement Guide 20 is inserted with the Distal Femoral Cutting Guide 30 into the IM Alignment Guide 6 until the Distal Femoral Cutting Guide 30 comes to rest on the anterior femoral cortex 140 (FIG. 17). With the IM Alignment Guide 6 base 9 flush against the distal condyles, the distal cutting slot 34 is positioned to remove the same amount of bone that will be replaced by the prosthetic femoral component. Pins are placed through the fixation hole 36 holes in anterior surface of the Distal Femoral Cutting Guide 30 to secure it further to the femur. The anterior thumb screw 38 is turned until it contacts the anterior femoral cortex 140 to further stabilize the cutting guide. The IM Alignment Guide 6 can be removed to ease cutting or it can be left in place if additional support is needed for the Distal Femoral Cutting Guide 30. If it is left in place, care should be taken to cut the bone all around the IM rod 4. The distal femur 142 is cut through the distal cutting slot 34. The valgus angle is now established.

Figure 18:
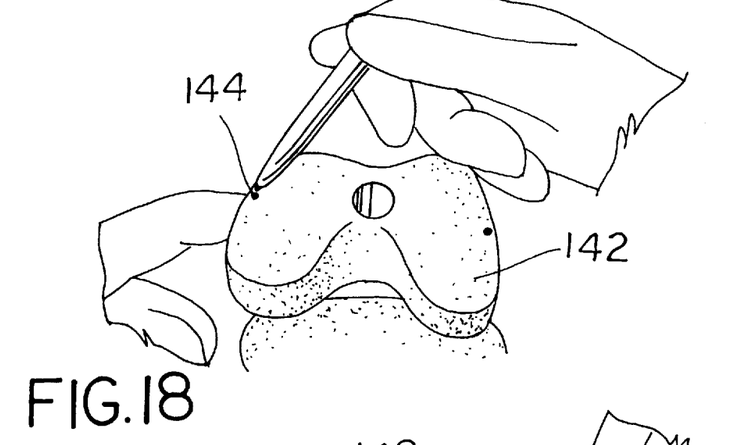
FIG. 18 is a perspective view of the distal femur showing how the epicondyles are palpated and marked.
Figure 19:
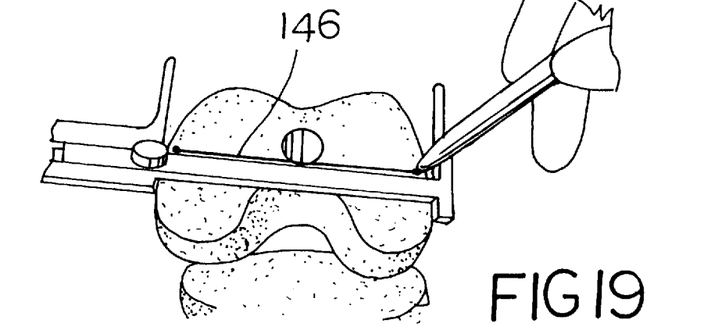
FIG. 19 is a perspective view of the distal femur showing how the epicondylar axis is marked.
Figure 20:
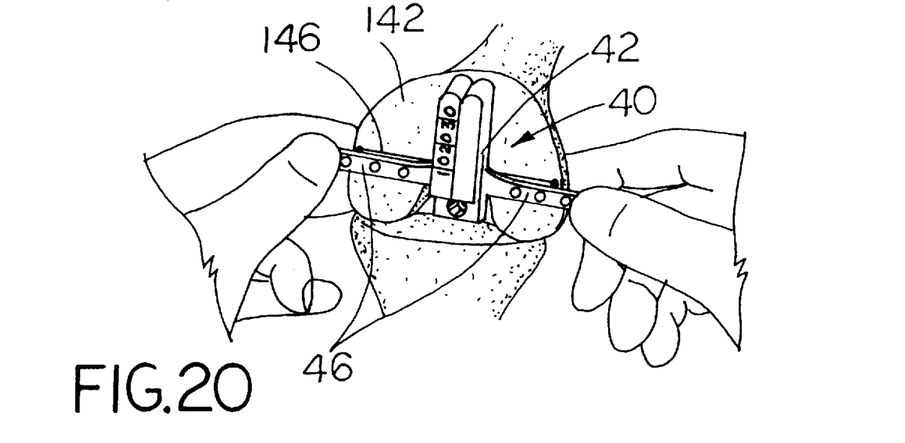
FIG. 20 is a perspective view of the Epicondylar Guide of FIG. 6 showing how it is placed on the distal femur in alignment with the epicondylar axis.
Figure 21:
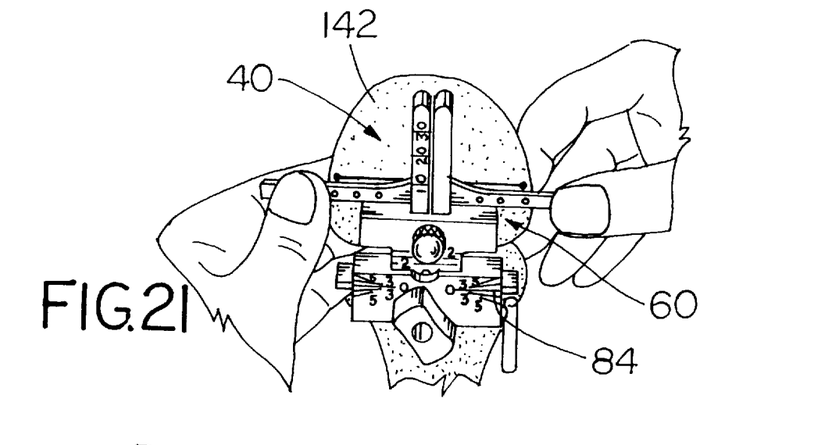
FIG. 21 is a perspective view of the Epicondylar Guide of FIG. 6 being used in conjunction with the Posterior Reference/Rotation Guide of FIG. 8.
Figure 22:
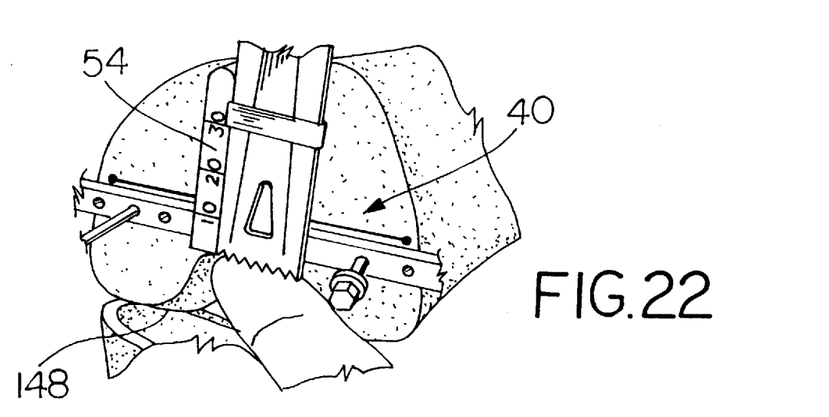
FIG. 22 is a perspective view of the Epicondylar Guide of FIG. 6 showing the use of the saw blade scale.
Figure 23:
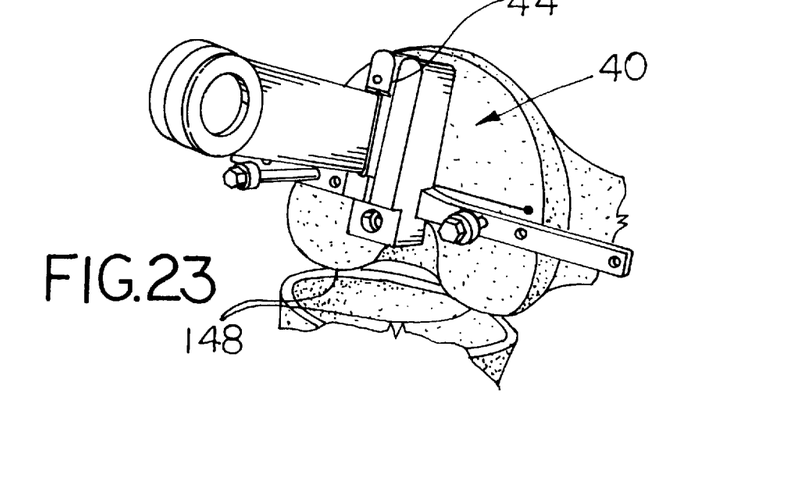
FIG. 23 is a perspective view of the Epicondylar Guide of FIG. 6 showing a slot being cut in the distal femur.

Next, femoral rotation is established as shown in FIGS. 18–24. Preferably the epicondyles are identified in order to determine the epicondylar axis which is the preferred indicator of proper external femoral rotation. The lateral epicondyle is identified by dissecting away the patellar femoral ligament. The medial epicondyle can be found by removing the synovium from the medial collateral ligament attachment on the femur. The location of the epicondyles can be marked on the distal femur 142 with methylene blue 144 (FIG. 18). A line drawn between these two marks represents the epicondylar axis 146 (FIG. 19). The Epicondylar Guide 40 is placed on the flat surface of the cut distal femur and the epicondyle reference arms 46 are aligned with the epicondylar axis (FIG. 20). The back 45 of the Epicondylar Guide 40 is flat so that it is stable as it rests on the flat cut distal femur 142. This also allows it to be slid and rotated about on the femur to achieve proper alignment. The central block 42 is small relative to the cut distal femur 142 so that the epicondylar axis 146 can be easily visualized. The epicondylar reference arms 46 are long and slender to enhance visualization and clearly indicate alignment of the Epicondylar Guide 40 With the epicondylar axis 146. The Epicondylar Guide 40 is then pinned in place. The amount of external rotation relative to the posterior condyles can be checked at this point as an additional verification of proper external rotation (FIG. 21). To do this the Posterior Reference/Rotation Guide 60 is attached to the Epicondylar Guide 40 and the feet are brought into contact with the posterior condyles 148. The amount of rotation relative to the posterior condyles is then read from the external rotation scale 84. If a valgus knee measures greater than 8° of rotation, or a varus knee greater than 5°, the Epicondylar Guide 40 should be reset within that range. A saw blade is marked at 30 mm to provide a 8 mm depth of cut by comparing the blade to the saw blade scale 54 provided on the Epicondylar Guide 40 (FIG. 22). Using the scale and marking the blade ensures a depth of cut that is not unnecessarily deep but that is deep enough to receive the fin 110 of the A/P Cutting Guide 90. A slot 150 is then cut in the distal femur through the A/P slot 44 in the Epicondylar Guide 40 to the depth marked on the blade (FIG. 23). The Epicondylar Guide 40 is then removed from the femur. The slot 150 cut into the distal femur establishes the external rotation for subsequent steps and allows A/P position to be set and fine tuned without the distraction of having to simultaneously set external rotation.

Figures 24, 25, 26, 27:
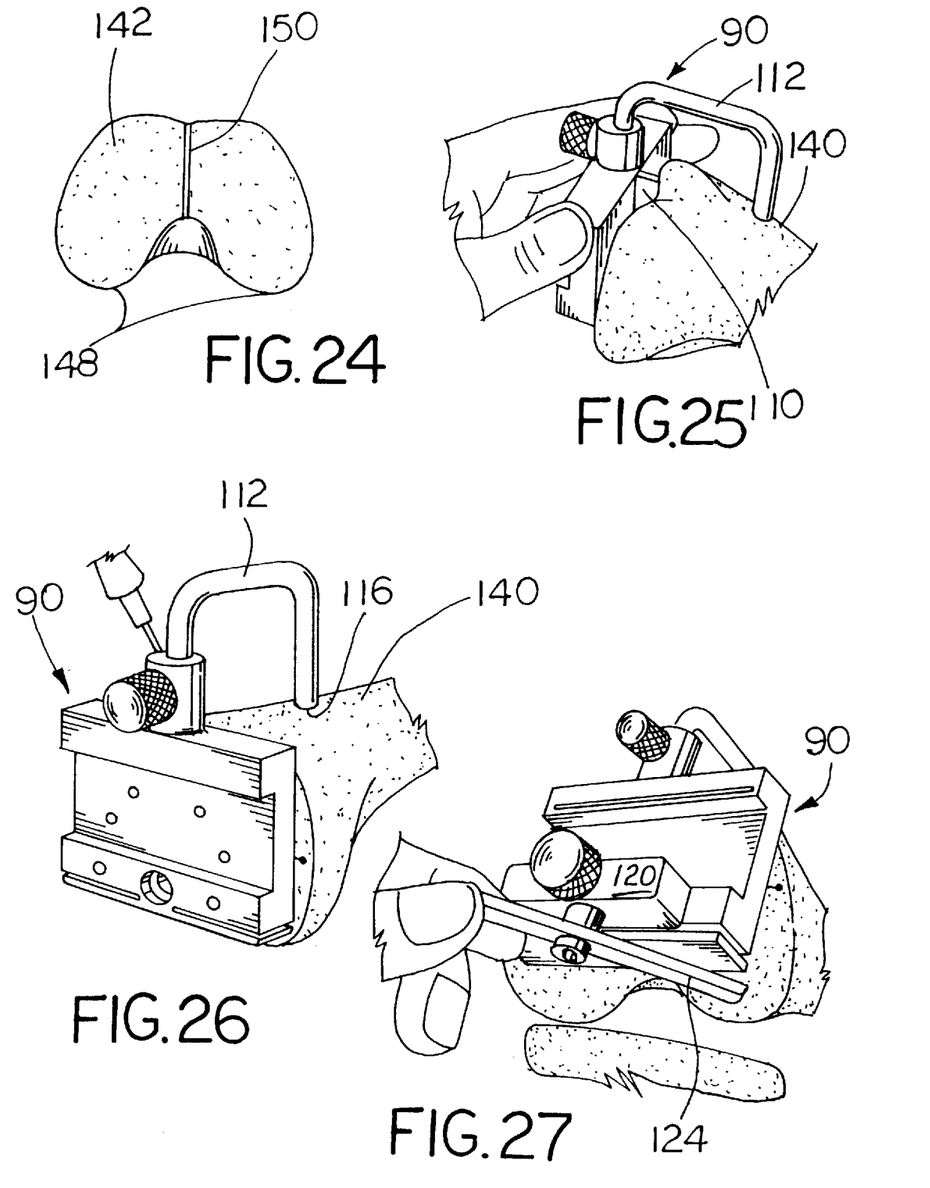
FIG. 24 is plan view showing the distal femur with the slot which was shown being cut in FIG. 23.
FIG. 25 is a perspective view of the A/P Cutting Guide of FIG. 11 being positioned on the distal femur.
FIG. 26 is a perspective view of the A/P Cutting Guide of FIG. 11 being positioned on the distal femur.
FIG. 27 is a perspective view of the Posterior Resection Gauge of FIG. 14 being used in conjunction with the A/P Cutting Guide of FIG. 11.

The A/P Cutting Guide 90 is placed on the distal femur 142 with its fin 110 engaging the slot 150 cut into the femur (FIG. 25). Preferably the fin 110 is sized to form a press fit in the slot 150 so that the surgeon can temporarily let go of the A/P Cutting Guide 90 without it falling off of the bone. The fin 110 and slot 150 engagement allows the A/P Cutting Guide 90 to be moved in the anterior and posterior directions without the A/P Cutting Guide 90 rotating. The A/P location of the A/P Cutting Guide 90 can be set by tapping the guide posteriorly until the probe end 116 of the anterior boom 112 contacts the anterior femoral cortex 140 (FIG. 27). The probe end 116 indicates the level of the anterior resection. The Posterior Resection Gauge 120 is attached to the A/P Cutting Guide 90 to indicate the posterior resection amount (FIG. 27). The position of the wing 124 indicates the position of the posterior condyles of the femoral component. Note that external rotation results in removal of more bone on the medial posterior condyle.

Figure 28:
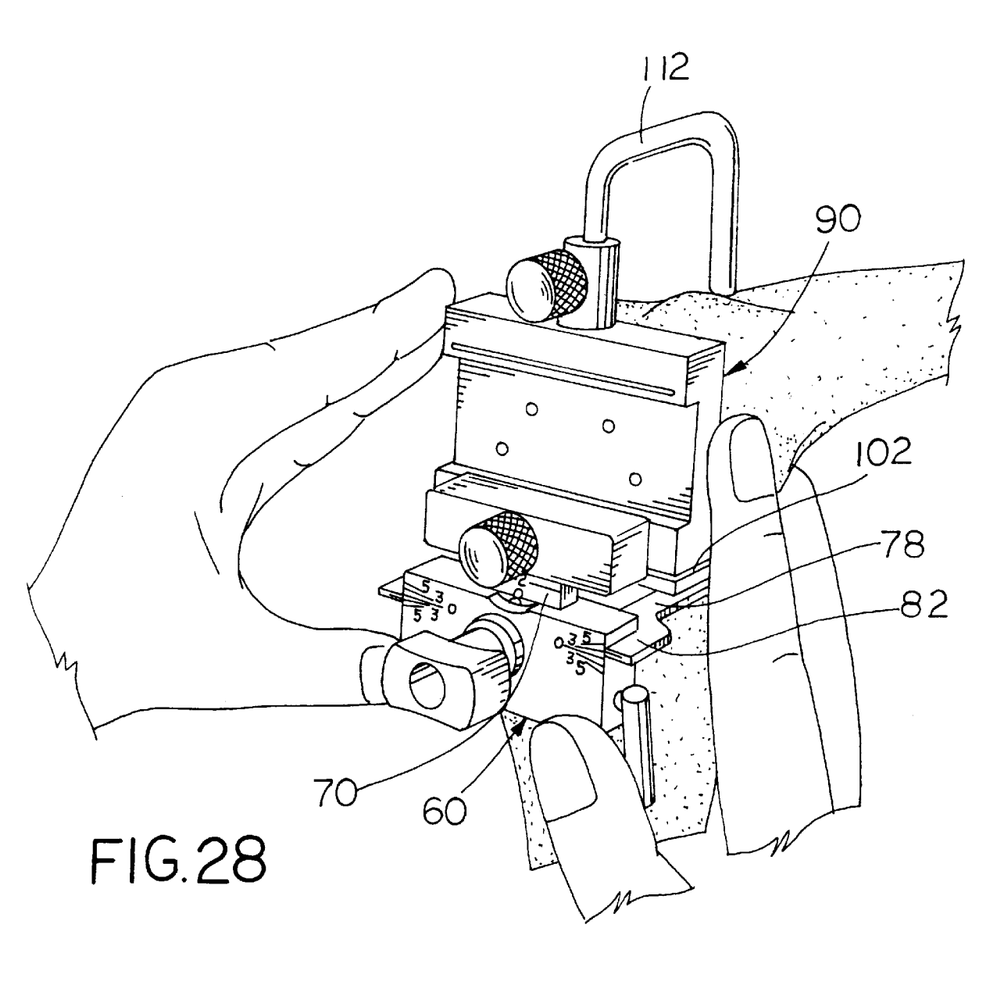
FIG. 28 is a perspective view of the Posterior Reference/Rotation Guide of FIG. 8 being used in conjunction with the A/P Cutting Guide of FIG. 11.

Alternatively, the Posterior Reference/Rotation Guide 60 may be used in place of the Posterior Resection Gauge 120 to verify femoral sizing and to check rotation (FIG. 28). First, the femoral position scale 70 on the Posterior Reference/Rotation Guide 60 is locked to the zero position. This zero setting ensures that when the feet 78 are flush with the posterior condyles, the amount of bone resected posteriorly will equal the posterior thickness of the implant. Thus the posterior condyles of the implant will be positioned where the natural posterior condyles were. This will produce the same flexion gap as the bone did. Note that external rotation results in removal of more bone on the medial posterior condyle. Next, the Posterior Reference/Rotation Guide 60 is attached to the A/P Cutting Guide 90. If the posterior condyles 148 prevent the guide from seating, because the anterior boom 112 is resting on the anterior femur and prevents the A/P Cutting Guide 90 from moving any further posteriorly, it will be necessary to unlock the femoral position scale 70. The resulting femoral position scale 70 reading represents the A/P position variance or the increase in flexion gap that will occur if the A/P Cutting Guide is positioned with the anterior boom. Another way of considering the information is that the femoral position scale 70 reading represents the variation from the standard posterior resection that will occur. For example, the 2 mm line below the zero setting would indicate that 2 mm additional posterior condyle bone would be resected. Stated another way, the flexion gap would be 2 mm larger than the extension gap. With this information, the A/P Cutting Guide 90 may be adjusted in order to minimize any potential imbalance in the flexion and extension gaps. For example, after swinging the anterior boom 112 out of contact with the anterior femur, the A/P Cutting Guide can be repositioned posteriorly to reduce the flexion gap. The preferable 3° distal flexion of the femur cut set with the Distal Femoral Cutting Guide 30 facilitates this adjustment and protects against notching of the femoral cortex.

Optionally, posterior referencing can be done first and the anterior boom used as a secondary check. In this case the Posterior Reference/Rotation Guide 60 is attached to the A/P Cutting Guide 90. The femoral position scale 70 is locked into the zero position. Both feet 78 of the Posterior Reference/Rotation Guide 60 are positioned in contact with the posterior condyles 148. The anterior placement of the guide is checked with the anterior boom 112 to ensure that femoral notching will not occur. The probe tip 116 of the anterior boom 112 indicates the level of the anterior resection. If the probe tip 116 indicates that notching of the femoral cortex may result, the femoral position scale 70 is unlocked and the A/P Cutting Guide 90 is adjusted anteriorly. The subsequent reading on the femoral position scale 70 represents the additional resection that will occur posteriorly to fit the femoral component.

Figure 29:
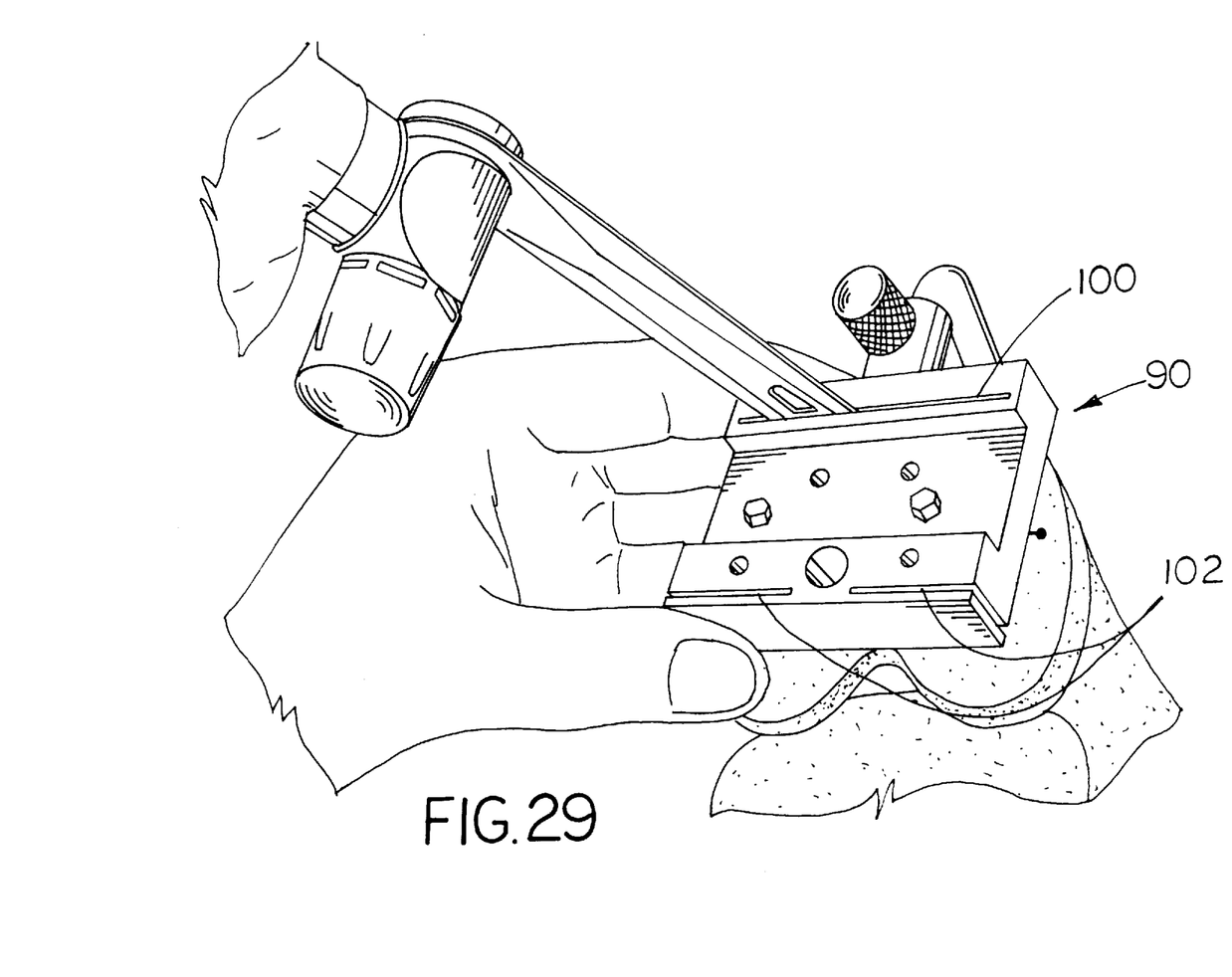
FIG. 29 is a perspective view of the A/P Cutting Guide of FIG. 11 being used to resect the anterior and posterior femoral condyles.

Once A/P placement has been decided, the A/P Cutting Guide 90 is pinned in place and the anterior and posterior femoral condyles are cut through the cutting slots 100 and 102 (FIG. 29). The valgus angle, external rotation and A/P placement of the femur have now each been independently and precisely determined. The final preparation of the femur and implantation of the femoral component can proceed according to standard techniques.

Figure 30:
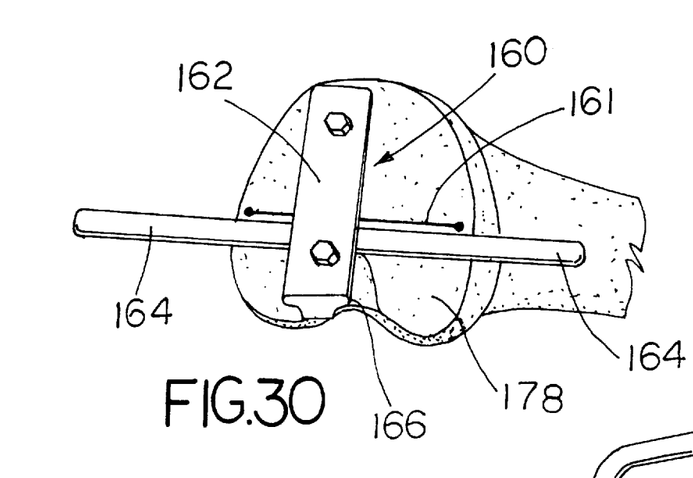
FIG. 30 is a perspective view of an alternative embodiment of an Epicondylar Guide.
Figure 31:
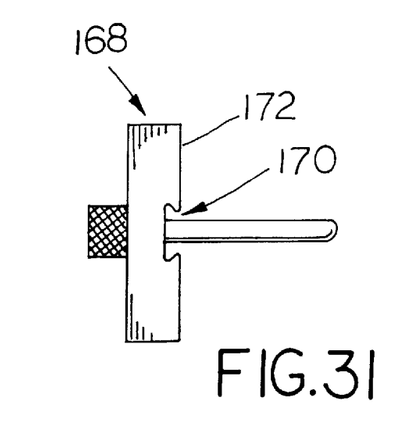
FIG. 31 is a bottom plan view of an alternative embodiment of an A/P Cutting Guide.
Figure 32:
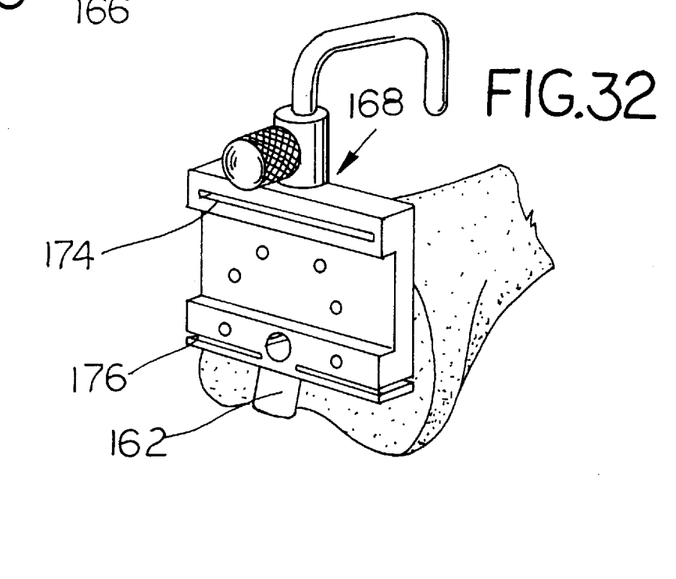
FIG. 32 is a perspective view of the A/P Cutting Guide of FIG. 31 in engagement with the Epicondylar Guide of FIG. 30.

FIGS. 30–32 depict alternative embodiments of the Epicondylar Guide and A/P cutting guide. The Epicondylar Guide 160 comprises a central block 162. A pair of arms 164 extends from the central block 162 to provide an axis for aligning the Epicondylar Guide 160 with the epicondylar axis 161. The arms 164 are preferably removably attached to the central block 162 such as by a threaded engagement. The central block 162 defines a linear track 166. The exemplary embodiment of FIG. 30 has a dove tail or T-shaped cross-section. The linear track 166 is perpendicular to the axis provided by the arms 164.

The A/P Cutting Guide 168 is configured generally like the A/P cutting Guide of FIGS.11–13. However, rather than having a fin like the embodiment of FIGS. 11–13, this alternative A/P Cutting Guide has a slot 170 formed in its back side 172. The slot 172 is perpendicular to the cutting slots 174 and 176. The slot 172 also is configured to engage the linear track 166. In use, the Epicondylar Guide 160 is positioned on the distal femur 178 and aligned with the epicondylar axis 161. The Epicondylar Guide 160 is then pinned in place and the arms 164 are removed. The A/P Cutting Guide 168 is placed with the slot 172 engaging the linear track 166. The A/P cutting Guide 168 is moved anteriorly and posteriorly along the linear track 166 until it is in the desired A/P position. The A/P Cutting Guide 168 is then pinned in place and the anterior and posterior femoral cuts are made.

It will be understood by those skilled in the art that the foregoing has described exemplary embodiments of the present invention and that variations may be made to these embodiments without departing from the spirit and scope of the invention defined by the appended claims. For example the exemplary embodiments depict a saw blade being used to make the anterior and posterior femoral cuts. However, the claimed methods and alignment guides could just as well be used with a milling system to resect the femoral bone. Such a milling system is taught in U.S. Pat. No. 5,474,559 issued to Bertin et al. and assigned to Zimmer, Inc. The present invention would be used for example to set the femoral bases of the femoral milling guide in the desired amount of rotation and in the desired A/P position.

What is claimed is:

1. A method for cutting a distal portion of a femur having anterior, posterior, medial and lateral aspects in preparation for implanting a prosthetic femoral component, the method comprising the steps of:

establishing a rotational reference on the distal femur, the rotational reference having a longitudinal axis located generally in the A/P direction;

engaging the rotational reference with an A/P cutting guide, the engagement between the A/P cutting guide and the rotational reference preventing rotation of the A/P cutting guide relative to the rotational reference and constraining the A/P cutting guide to motion along the longitudinal axis of the rotational reference;

adjusting the A/P cutting guide along the longitudinal axis until it is in a desired A/P position; and cutting the anterior and posterior portions of the distal femur by referencing the A/P cutting guide.

2. The method of claim 1 wherein the step of establishing a rotational reference on the distal femur further includes the steps of:

placing a rotation guide on the distal femur;

orienting the rotation guide to a desired rotational position, the rotation guide having a longitudinal axis that extends in a generally A/P direction on the distal femur.

3. The method of claim 2 wherein, in the step of engaging the rotational reference with the A/P cutting guide, the A/P cutting guide engages the rotation guide.

4. The method of claim 1 wherein the step of establishing a rotational reference on the distal femur further includes the steps of:

placing a rotational guide on the distal femur;

orienting the rotational guide to a desired rotational position;

cutting a slot in the distal femur by referencing the rotational guide, the slot extending in a generally A/P direction on the distal femur.

5. The method of claim 4 wherein the A/P cutting guide has a portion that extends into the slot to constrain the A/P cutting guide to motion along the length of the slot, and the step of engaging the rotational reference with an A/P cutting guide includes placing the portion in the slot.

6. The method of claim 1 wherein the step of establishing the rotational reference includes the steps of locating the femoral epicondyles and orienting the rotational reference so that it is perpendicular to a line between the epicondyles.

7. The method of claim 1 further including, before the step of establishing a rotational reference, the step of cutting the distal femur to provide a flat distal surface.

8. The method of claim 7 wherein the distal femur is cut at approximately 3 degrees of flexion.

9. The method of claim 1 further including, after the step of establishing a rotational reference on the distal femur, the steps of providing a posterior reference guide having extending feet, contacting the posterior condyles with the feet, and reading the amount of rotation of the rotation guide relative to the posterior condyles from an external rotation scale on the posterior reference guide.

10. The method of claim 1 further including, after the step of engaging the rotational reference with an A/P cutting guide, the step of checking the posterior resection amount with a posterior resection gauge attached to the A/P cutting guide.

11. The method of claim 1 further including, after the step of engaging the rotational reference with an A/P cutting guide, providing a posterior reference guide having extending feet, contacting the posterior condyles with the feet, reading the amount of A/P position variance from an A/P position variance scale, and adjusting the A/P cutting guide to produce the desired flexion gap.

12. An A/P cutting guide for guiding a cutting instrument to cut a distal portion of a femur having anterior, posterior, medial and lateral aspects, the distal portion of the femur having a slot cut into it to established thereon a rotational reference, the A/P cutting guide comprising:
  a body;
  guiding means connected to the body for establishing anterior and posterior cutting planes for the cutting instrument;
  engagement means connected to the body for engaging the rotational reference, the engagement means cooperating with the rotational reference to prevent rotation of the body relative to the rotational reference and the engagement means cooperating with the rotational reference to permit translation of the body on the distal femur back and forth between the anterior and posterior aspects of the distal femur, the engagement means comprising a fin extending from the body.

13. The combination of a rotation guide for establishing a rotational reference on a distal portion of a femur and an A/P cutting guide for guiding a cutting instrument to cut a distal portion of a femur having anterior, posterior, medial and lateral aspects, the combination comprising:
  a rotation guide having a central block having front and back surfaces;
  a rotational reference extending from the front surface, the rotational reference defining a linear track;
  a slender elongated reference arm extending from the block perpendicular to the linear track;
  an A/P cutting guide having a body, the body including a slot in engagement with the linear track; and
  guiding means connected to the body for establishing anterior and posterior cutting planes for the cutting instrument;
the slot cooperating with the linear track to prevent rotation of the body relative to the rotational reference and the slot cooperating with the linear track to permit translation of the body on the distal femur back and forth between the anterior and posterior aspects of the distal femur.

14. A rotation guide for establishing a rotational reference on a distal portion of a femur, the rotation guide comprising:
  a central block having front and back surfaces and an elongated slot extending through the block from the front surface to the back surface;
  a slender elongated reference arm extending from the block perpendicular to the slot;
  a neck extending from the block;
  a sliding member in sliding engagement with the neck, the sliding member being slidable from a first position on the neck to a second position on the neck, the first position being nearer to the block than the second position;
  an A/P position scale on the rotation guide for indicating the position of the sliding member relative to the block;
  a foot extending from the sliding member, the foot being mounted for rotation relative to the sliding member;
  an external rotation scale on the rotation guide for indicating how much the foot is rotated relative to the sliding member.

15. An A/P cutting guide for guiding a cutting instrument to cut a distal portion of a femur having anterior, posterior, medial and lateral aspects, the distal portion of the femur having established thereon a rotational reference, the A/P cutting guide comprising:
  a body;
  guiding means connected to the body for establishing anterior and posterior cutting planes for the cutting instrument;
  engagement means connected to the body for engaging the rotational reference, the engagement means cooperating with the rotational reference to prevent rotation of the body relative to the rotational reference and the engagement means cooperating with the rotational reference to permit translation of the body on the distal femur back and forth between the anterior and posterior aspects of the distal femur;
  a neck extending from the body;
  a sliding member in sliding engagement with the neck, the sliding member being slidable from a first position on the neck to a second position on the neck, the first position being nearer to the body than the second position;
  an A/P position scale on the A/P cutting guide for indicating the position of the sliding member relative to the body;
  a foot extending from the sliding member, the foot being mounted for rotation relative to the sliding member;
  an external rotation scale on the A/P cutting guide for indicating how much the foot is rotated relative to the sliding member.

* * * * *